United States Patent [19]

Colvin

[11] Patent Number: 5,014,011
[45] Date of Patent: May 7, 1991

[54] CAPACITANCE MEASURING APPARATUS WITH MEANS FOR NULLING THE RESISTIVE COMPONENT

[75] Inventor: Alex D. Colvin, Oak Park, Mich.

[73] Assignee: Ford Motor Company, Dearborn, Mich.

[21] Appl. No.: 200,284

[22] Filed: May 31, 1988

[51] Int. Cl.$^5$ ............................................. G01R 27/26
[52] U.S. Cl. ....................................... 324/663; 324/658
[58] Field of Search ................. 324/61 R, 60 R, 60 C; 73/61 R, 61.1 R

[56] References Cited

U.S. PATENT DOCUMENTS

| | | | |
|---|---|---|---|
| 3,486,108 | 12/1969 | Rosica et al. | 324/61 R |
| 3,947,760 | 3/1976 | Noguchi et al. | 324/57 R |
| 4,288,741 | 9/1981 | Dechene et al. | 324/61 R |

OTHER PUBLICATIONS

IEEE Transactions on Vehicular Technology, vol. VT-27, No. 3, Aug. 1978, p. 142, "An On-Board Sensor For Percent Alcohol", Hille et al.

Primary Examiner—Reinhard J. Eisenzopf
Assistant Examiner—Anthony L. Miele
Attorney, Agent, or Firm—Allan J. Lippa; Peter Abolins

[57] ABSTRACT

A circuit and method for measuring the capacitance of a medium independent of the resistivity of the medium. A triangular voltage is applied to plates immersed in the medium to generate both a resistive current component in phase with the triangular voltage and a capacitive current component in phase with a differential of the triangular voltage. The resistive and capacitive current components are summed with a selectable current which is provided having a phase $\pi$ radians out of phase with the triangular voltage and having an amplitude related to a control signal. The summed current is sampled over a time period phase shifted from the capacitive current component and then integrated so that the capacitive current component integrates to zero and the integral of the resistive current component minus the selectable current provides the control signal. In response to the control signal, the selectable current is varied until the sum of the selectable current and resistive current component are nulled. This summed current is then sampled in phase with the capacitive current component thereby obtaining a measurment of capacitance independent of resistance.

4 Claims, 4 Drawing Sheets

# 5,014,011

CAPACITANCE MEASURING APPARATUS WITH MEANS FOR NULLING THE RESISTIVE COMPONENT

BACKGROUND

The field of the invention relates to the measurement of capacitance, in particular the measurement of lossy capacitance. Stated another way, the measurement of capacitance shunted by a low resistance.

As the world's petroleum reserves become depleted, interest has increased in adapting vehicles to run on a mixture of gasoline and alcohol (including ethanol and methanol). With present technology, vehicles may be adapted to run on a gasoline/alcohol mixture by altering the engine's air/fuel ratio and/or ignition timing to compensate for the lower energy density of these fuel mixtures. Since the fuel mixture may vary depending upon both gasoline and alcohol availability in a specific locality, it is desirable to have an on-board sensor for providing an engine controller with an indication of gasoline/alcohol mixture in the fuel tank.

Gasoline and alcohol have substantially different dielectric constants. Accordingly, measurement of the capacitance between two parallel plates suspended in the fuel tank may provide an approximation of the gasoline/alcohol mixture. However, the gasoline/alcohol mixture contains contaminants, such as sodium or calcium ions, from dessicants, thereby adding a resistive component between the plates. This parallel resistive component may be sufficiently low to overwhelm capacitive measurement unless very high frequencies, such as 10 MHz, are used. For example, when measured at 30 KHz, the resistive current component between the plates may be approximately 20 times greater than the capacitive current component.

A prior approach for on-board measurement is disclosed in *IEEE Transactions on Vehicular Technology*, Volume VT-27, No. 3, August 1978, page 142, entitled "An On-Board Sensor For Percent Alcohol", by J. W. Hille and P. R. Rabe. This approach requires a tuned circuit for comparing the capacitance to be measured to a calibrated reference. A disadvantage with this approach is that variations in the reference will adversely affect the measurement. Further, the problem of a high resistive current component does not appear to be addressed.

An approach to measurement of capacitance in general, rather than the capacitance of a gasoline/alcohol mixture, is disclosed in U.S. Pat. No. 3,947,760. A circuit is disclosed for measuring both the resistance and capacitance of a capacitor. The ratio of charging and discharging times of two integrative capacitors is compared to determine the desired measurements. This circuit has the disadvantage of requiring a variable voltage source. In addition, the problem of a high resistive component overwhelming the capacitive current component does not appear to be addressed.

SUMMARY OF THE INVENTION

An object of the invention described herein is to provide both an apparatus and a method for accurately measuring capacitance having a low shunting resistance.

The above problems and disadvantages are overcome, and object achieved by the apparatus and method described herein for measuring the capacitance of a medium independently of the resistivity of the medium.

In one aspect of the invention, the apparatus comprises: means for applying a periodic voltage to plates immersed in the medium to generate both a resistive current component flowing through the medium in phase with the periodic voltage and a capacitive current component flowing through the medium in phase with a time derivitive of the periodic voltage; current providing means coupled to both the periodic voltage and a control signal for providing a selectable current $\pi$ radians out of phase with the periodic voltage and having an amplitude related to the control signal; current summing means coupled to both the medium and the current providing means for summing the selectable current and the resistive current component and the capacitive current component; sampling means for sampling the summed current over a time period in phase with the resistive current component; averaging means coupled to the sampling means for averaging the capacitive current component to zero and for averaging the resistive current component minus the selectable current to generate the control signal; means for coupling the control signal to the current providing means so that the current providing means provides the selectable current substantially equal to the resistive current component and $\pi$ radians out of phase with the resistive current component thereby nulling the resistive current component from the summed current; and detecting means coupled to the summing means and in phase with the capacitive current component for detecting the capacitive current component independently of the resistive current component.

By nulling the resistive current component, as described hereinabove, an advantage is obtained of obtaining a measurement of the capacitive current component which would otherwise be overwhelmed by the resistive current component. An additional advantage is that an accurate measurement of capacitance is obtained without the need of an accurately calibrated reference. A further advantage is that a variable source of periodic voltage is not required. Still another advantage obtained is that a high frequency periodic voltage is not required.

In another aspect of the invention, an accurate measurement of the alcohol/gasoline fuel mixture in an automobile is provided by measuring the capacitance between two plates in the fuel mixture independently of the resistivity of the fuel mixture. More specifically, this apparatus comprises: a voltage source applying a periodic voltage accross parallel capacitive plates positioned in the mixture to generate both a resistive current component in phase with said periodic voltage and a capacitive current component in phase with a time derivitive of said periodic voltage; a current generator coupled to both the periodic voltage and a control signal for providing a selectable current $\pi$ radians out of phase with the periodic voltage and having an amplitude related to the control signal; current summing means coupled to both the parallel plates and the current generator for summing the selectable current and the resistive current component and the capacitive current component; sampling means for sampling the summed current over a time period in phase with the resistive current component; an integrator coupled to the sampling means for integrating the capacitive current component to zero and for integrating the resistive current component plus the selectable current to define the control signal; a feedback loop for coupling the control signal to the current generator so that the current generator provides the selectable current substantially equal to the resistive current component and $\pi$ radians out of phase with the resistive current component thereby nulling the resistive current component from the summed current; measuring means coupled to the summing means and in phase with the capacitive current component for measuring the capacitive current component independently of the resistive current component; and means for converting the measurement of said capacitive current component into an indication of the alcohol/gasoline fuel mixture.

BRIEF DESCRIPTION OF THE DRAWINGS

The invention will now be further described, by way of example, with reference to the accompanying drawings, in which.

DESCRIPTION OF THE PREFERRED EMBODIMENT

Figure 1:
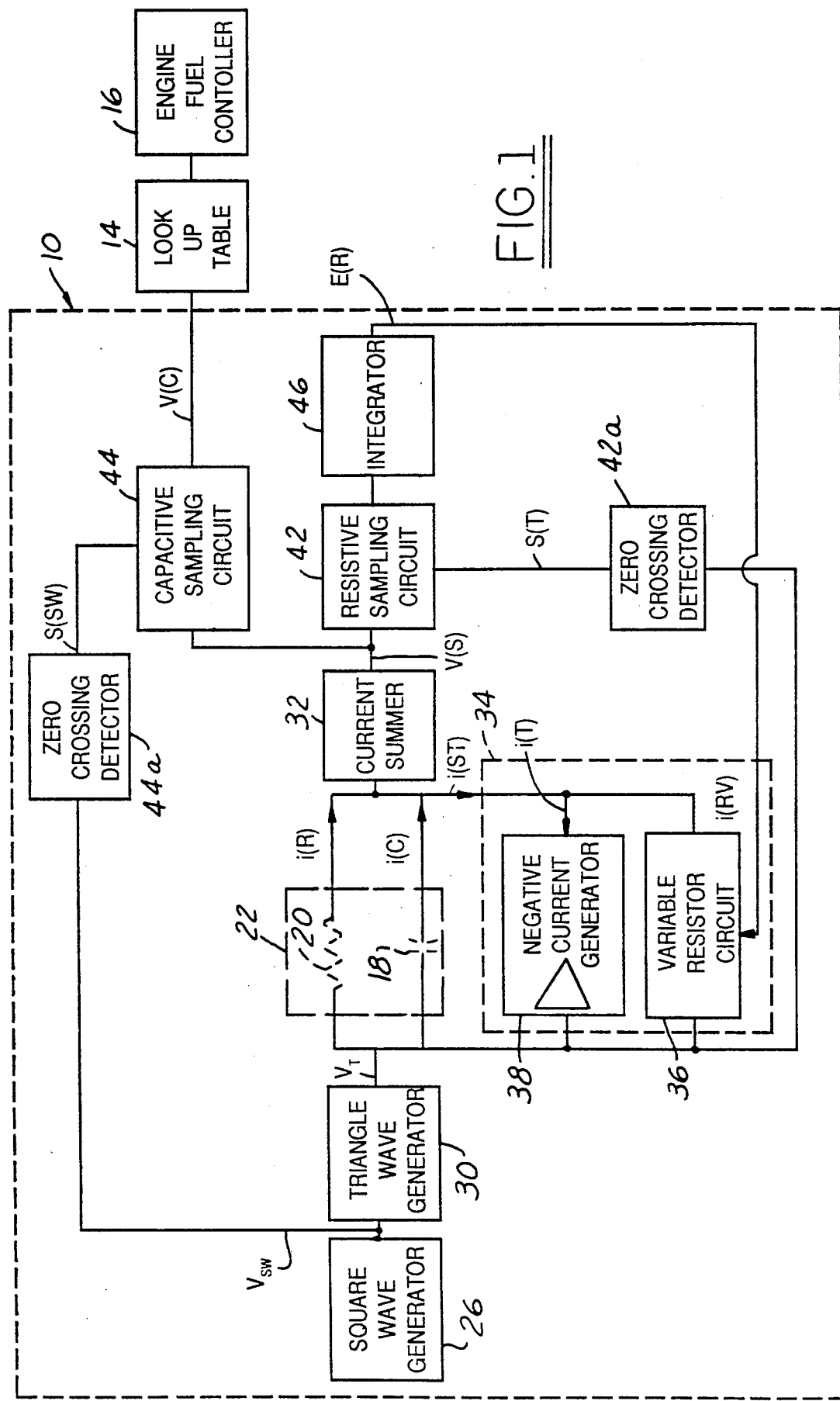
FIG. 1 is an electronic block diagram of an embodiment in which the invention is used to advantage.
Figure 2:
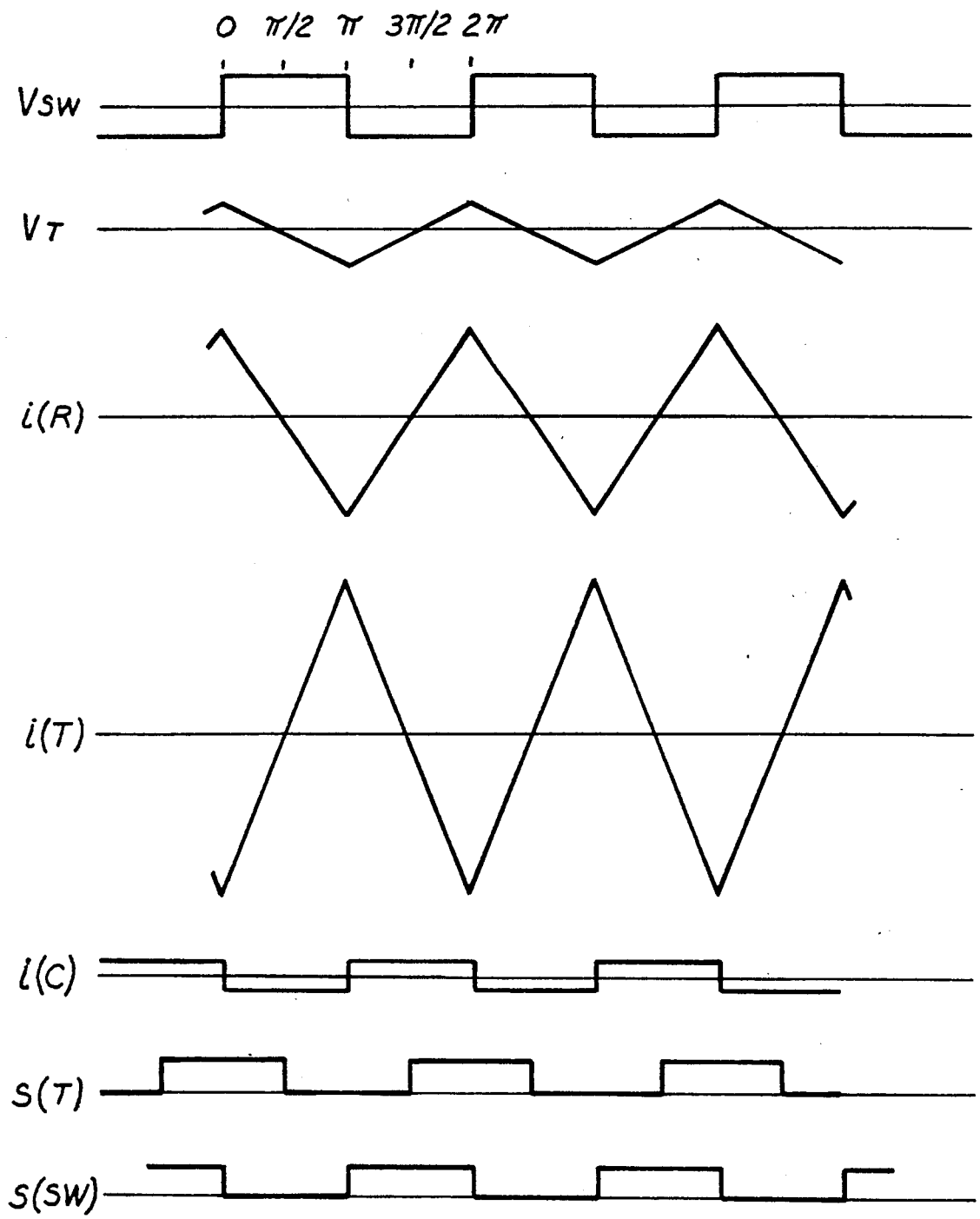
FIGS. 2 and 3 show various electronic waveforms associated with FIGS. 1 and 4.

Referring first to FIGS. 1 and 2, a block diagram (FIG. 1) and associated electrical signal wave forms (FIG. 2) illustrate an example of one circuit wherein the invention is used to advantage. More specifically, capacitance measuring circuit 10 is shown for measuring the capacitance of a gasoline/alcohol fuel mixture in the fuel tank (not shown) of a motor vehicle. In response to the measurement of capacitance, look up table 14 provides engine fuel controller 16 with a measurement of the alcohol content of the gasoline/alcohol fuel mixture for proper air/fuel ratio control. Since the dielectric constant of alcohol is approximately an order of magnitude greater than the dielectric constant of gasoline, an accurate measurement of capacitance is converted, by look up table 14, into a measurement of the alcohol content of the gasoline/alcohol fuel mixture.

Capacitor 18 and resistor 20 schematically illustrate the respective capacitance and shunt resistance between two spaced capacitive parallel plates 22 having a medium therebetween. In this example, the medium is the gasoline/alcohol fuel mixture. Resistor 20 is representative of the resistance caused by contaminants such as sodium or calcium ions in the fuel mixture. These contaminants may have sufficient concentration to render the fuel mixture conductive. For example, measurements by the inventor herein have indicated that 800 ohms is not unusual for a 10 picofarad capacitor. Measurements have also indicated that the resistive current component can be approximately 20 times greater than the capacitive current component. Accordingly, previous approaches to measuring the capacitance of capacitor 18 have been frustrated by the resistive current component. As described in greater detail hereinafter, capacitive measuring circuit 10 solves the problem of providing an accurate measurement of capacitance when shunted by a low resistance.

Continuing with FIGS. 1 and 2, a general description of circuit 10 is presented. A more detailed description of circuit 10 is provided hereinafter with particular reference to FIG. 3. Conventional square wave generator 26 provides a voltage square wave $V_{SW}$ to triangular wave generator 30. Square wave $V_{SW}$ is integrated by triangular wave generator 30 to generate a triangular voltage wave $V_T$. It is seen that the zero crossings of $V_T$ are $\pi/2$ radians shifted from the zero crossings of $V_{SW}$. Stated another way, $V_T$ is $\pi/2$ radians out of phase with $V_{SW}$.

$V_T$ is shown applied across capacitive plates 22 immersed in the gasoline/alcohol mixture. Capacitive plates 22 are schematically shown represented as capacitor 18, with a dielectric constant determined by the percent of alcohol in the gasoline/alcohol mixture, and a parallel shunt resistor 20. In response to $V_T$, resistive current component i(R) through resistor 20 and capacitive current component i(C) are generated. Resistive current component i(R) is in phase with $V_T$ and capacitive current component i(C) is essentially the time derivitive of $V_T$. That is, i(C) is proportional to d $V_T/d(T)$. Accordingly, i(C) is essentially a square wave having zero crossings in phase with the directional changes of $V_T$. It is to be noted that the relative amplitudes shown in FIG. 2 are not to scale. For example, as stated previously herein, resistive current component i(R) may be approximately 20 times greater than capacitive current component i(C).

In general terms, resistive current component i(R) and capacitive current component i(C) are summed in current summer 32 with a selectable current i(ST) from current providing circuit 34. Selectable current i(ST) is $\pi$ radians out of phase with resistive current component i(R) and has an amplitude which varies with electronic control signal E(R). For reasons described herein after, E(R) is generated through a feedback loop for nulling resistive current component i(R).

More specifically, current providing circuit 34 is shown having $V_T$ applied across it and is also shown including, in this particular example, the parallel combination of variable resistor 78 and negative current generator 38. The resistance of variable resistor 78, RV, varies in proportion to the amplitude of E(R). Since $V_T$ is applied across variable resistor 36, variable current i(RV) therethrough is a function of both VT and E(R), and in phase with $V_T$. Negative current generator 38 provides negative current i(T) shown $\pi 0$ radians out of phase with $V_T$ and, accordingly, i(R). Thus, selectable current i(ST) = i(RV) − i(T).

Figure 3:
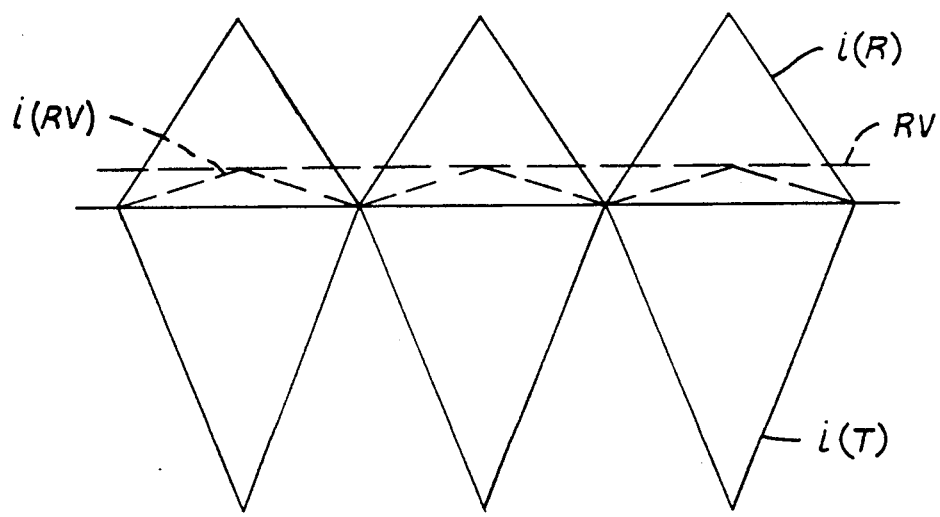

Continuing with FIG. 1, and also referring to FIG. 3, the output of current summer 32 is a voltage V(S) proportional to the summed current i(S) where i(S) = i(R) + i(C) − i(T) + i(RV). The output of current summer 32 is coupled to both resistive sampling circuit 42 and capacitive sampling circuit 44. Resistive sampling circuit 42 samples i(S) in phase with the zero crossings of $V_T$ as determined by sampling signal S(T) from zero crossing detector 42A. The sampled summed current is then integrated in integrator 46, the integral thereof defining E(R). Since capacitive current component i(C) is essentially a square wave having zero crossing points $\pi/2$ radians out of phase with S(T), capacitive current component i(C) will integrate to zero. Accordingly, E(R) represents the integral of the summed current components without capacitive current component i(C) as follows:

$$E(R) = \int i(R) + i(RV) - i(T) \, dt$$

In response to E(R), variable resistance RV of variable resistor 36 is changed such that i(R) + i(RV) − i(T) = zero. This is diagramatically shown in FIG. 3. After the above steady state operation is achieved, summed current i(S) is then equal to capacitive current component i(C). As previously described herein, resistive current component i(R) has been nulled so that an accurate measurement of capacitive current component i(C) and, accordingly, the capacitance of the gasoline/alcohol mixture, is obtained. Continuing with FIG. 1, capacitive sampling circuit 44 samples summed current i(S) in phase with sampling signal S(SW) from zero crossing detector 44. Sampling signal S(SW) is in phase with the change in direction of $V_T$ and, accordingly, in phase with capacitive current component i(C). The output of capacitive sampling circuit 44 is a voltage V(C) having an amplitude directly proportional to the capacitance of the medium measured, in this case the gasoline/alcohol mixture. Continuing with this illustrative use of capacitive measuring circuit 10, V(C) is converted by look up table 14 into an indication of the alcohol content of the gasoline/alcohol mixture for use by engine fuel controller 16. Since alcohol has a lower energy density than gasoline, engine fuel controller 16 increases the fuel delivered to the internal combustion engine (not shown) as a function of the alcohol content in the gasoline/alcohol mixture.

In view of the above, it is seen that an advantage is obtained of providing an accurate measurement of capacitance by nulling out the resistive current component. Otherwise, in applications where the resistive current component is significantly larger than the capacitive current component, an acceptable measurement of the capacitive current component would not be obtainable. A further advantage is obtained because the high frequencies used in prior approaches to obtain a measurement of capacitance are not required here. In one application in which the invention was used to advantage, a 30 KHz square wave generator was used. With the low frequencies utilized, as compared to prior approaches, less expensive electronic components are used. For example, referring to the detailed electronic schematic shown in FIG. 4, nine conventional operational amplifiers are used.

Figure 4:
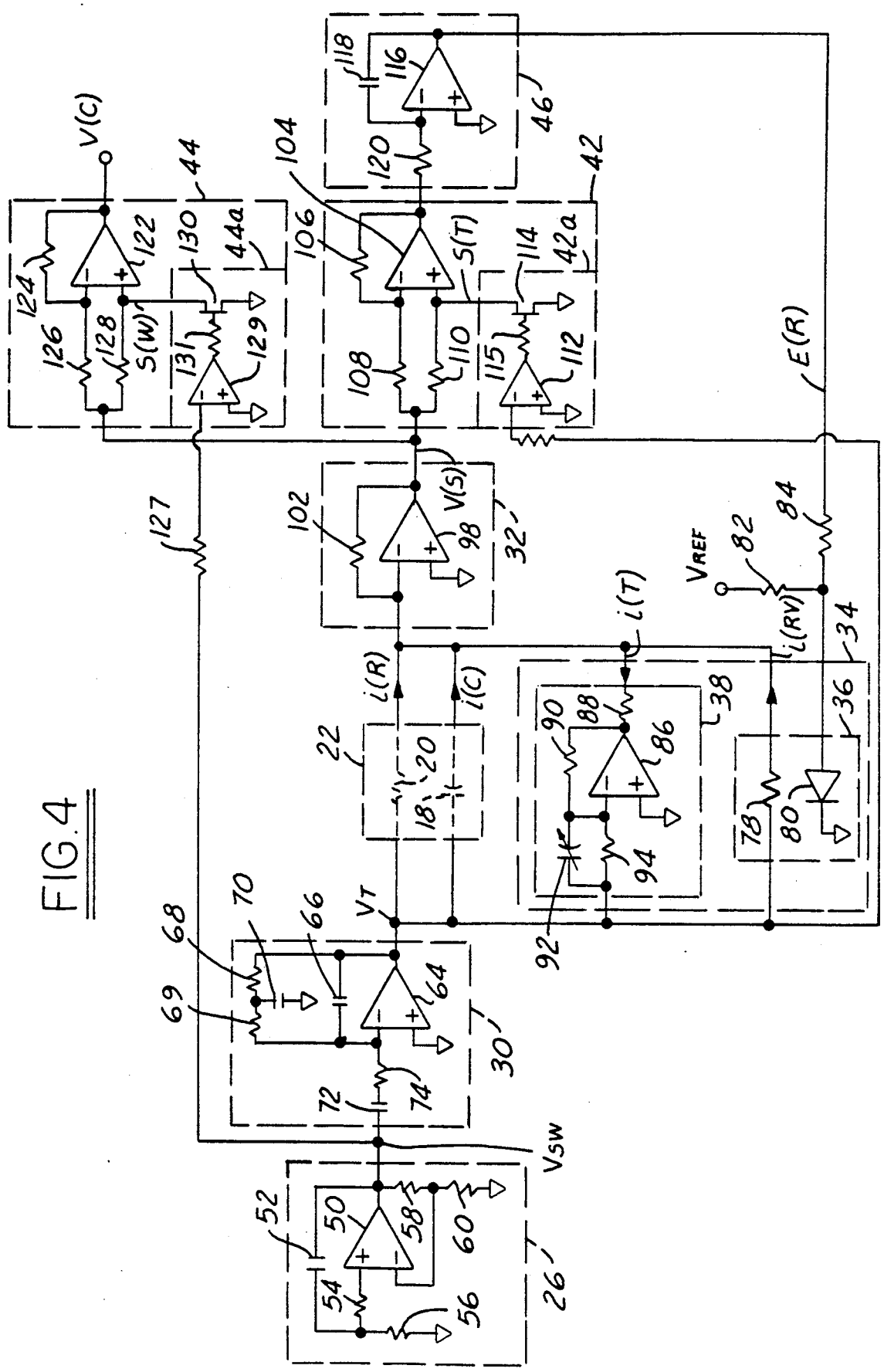
FIG. 4 is a schematic of electronic circuits associated with the block diagram of FIG. 1.

Referring now to FIG. 4 wherein like numerals refer to like parts shown in FIG. 1, a detailed example of a circuit which may be used to advantage for capacitance measurement circuit 10 is shown. Square wave generator 26 is shown in this example as a square wave oscillator including operational amplifier 50 having feedback to the positive input terminal through capacitor 52 and a resistive voltage divider defined by resistors 54 and 56. Feedback is also shown to the negative input terminal through a resistive voltage divider defined by resistors 58 and 60. Triangular wave generator 30 is shown in this example as an integrator circuit including operational amplifier 64 for integrating V(SW) from square wave generator 26 to generate $V_T$. Operational amplifier 64 is shown configured as an integrator with feedback through capacitor 66. A conventional DC eliminator shown defined by resistors 68 and 69, and capacitor 70, is shown as another feedback loop to eliminate the DC component. Capacitor 72 is shown coupled to the negative input terminal for DC blocking.

Variable resistor circuit 36 of current providing circuit 34 is shown as resistor 78, having a light sensitive resistance, optically coupled to optical diode 80 which is responsive to electronic control signal E(R). Voltage translation of E(R) is shown through a conventional resistive voltage divider, resistors 82 and 84, coupled to a supply voltage $V_{Ref}$. Negative current generator 38, of current providing circuit 34, is shown as conventional operational amplifier 86, configured as a phase inverter with gain provided by the ratio of feedback resistor 90 to negative input resistor 94. Adjustable capacitor 92, shown connected parallel to input resistor 94, aligns the phase of a negative current i(T) from operational amplifier 86 with $V_T$. Resistor 88 is shown to convert the voltage output of operational amplifier 86 to i(T).

Current sensing means 32 is shown as operational amplifier 98 having feedback resistor 102 coupled to the negative input terminal. In a conventional manner, the negative input terminal acts as a virtual ground wherein i(R), i(C), i(T), and i(RV) are summed. Operational amplifier 98 also acts as a current to voltage converter providing an output voltage V(S) directly related to the summed currents to resistive sampling circuit 42.

Resistive sampling circuit 42 is shown including operational amplifier 104 having feedback resistor 106, negative input resistor 108, positive input resistor 110, and zero crossing detector 42A coupled to the positive input terminal. Zero crossing detector 42A is shown including operational amplifier 112 with a negative input coupled to $V_T$ and an inverted output coupled to the gate of FET 114. Sampling signal S(T) is provided by coupling ground to the positive input terminal of operational amplifier 104 through FET 114 in response to $V_T$. In accordance with the above description, sampling signal S(T) is $\pi$ radians phase shifted from $V_T$ and switches at the zero crossings of $V_T$. Thus, the output of resistive sampling circuit 42 is phase inverted from V(S) when S(T) is shorted to ground and its output is directly related to V(S) when S(T) is floating.

Referring to FIGS. 2 and 3, resistive sampling circuit 42 positively rectifies i(R) and i(RV), and negatively rectifies i(T). Since i(C) is $\pi/2$ radians phase shifted from S(T), i(C) is integrated to zero by integrator 46.

Referring back to FIG. 4, integrator 46 is shown as a conventional operational amplifier 116 configured as an integrator with feedback capacitor 118 and negative input resistor 120. Since integrator 46 nulls capacitive current component i(C), the output of integrator 46 is therefore representative of the integral, ER, of the remaining recitified currents: i(RV) + i(R) − i(T). As previously discussed, variable resistance RV is varied in response to ER so that i(RV) + i(R) − i(T) = zero.

The output of current summing means 32 is also coupled to capacitive sampling circuit 44. This circuit is shown including operational amplifier 122 having feedback resistor 124, negative input resistor 126, positive input resistor 128 and zero crossing detector 44A coupled to the positive input terminal of operational amplifier 122. Zero crossing detector 44A is shown having operational amplifier 129 with an negative input coupled to $V_{SW}$ and output coupled to the gate of FET 130. Sampling signal S(W) is provided by a coupling ground to the positive input terminal of operational amplifier 122 through FET 130 in response to $V_{SW}$. Accordingly, sampling signed S(W) is $\pi$ radians phase shifted from $V_{SW}$.

When S(W) is shorted to ground, capacitive sampling circuit 44 inverts V(S), and when S(W) is floating, capacitive sampling circuit 44 passes V(S) through resistors 124 and 126. Since S(W) is in phase with i(C), and i(R) has been nulled as previously described, the output of capacitive sampling circuit 44 is a voltage related to the capacitive current component i(C).

This concludes the description of the preferred embodiment. The reading of it by those skilled in the art will bring to mind many alterations and modifications without departing from the spirit and scope of the invention. For example, although analogue components, such as operational amplifiers, are shown in the detailed electrical schematic presented in FIG. 4, those skilled in the art will recognize that other circuits may be used such as digital circuits with appropriate sampling signals. Accordingly, it is intended that the scope of the invention be limited only by the following claims.

I claim:

1. An apparatus for measuring the capacitance of a medium independently of the resistivity of the medium, comprising:

means for applying a periodic voltage to the medium to generate both a resistive current component flowing through the medium in phase with said periodic voltage and a capacitive current component flowing through the medium in phase with a time derivative of said periodic voltage;

a negative current generator coupled to said periodic voltage applying means for generating a negative current proportional to and $\pi$ radians out of phase with said periodic voltage independently of the medium, said current generator including phase alignment means for aligning phase transitions of said negative current with phase transitions of said periodic voltages;

a variable light sensitive resistor coupled to said periodic voltage and having a resistive value proportional to amplitude of a radiant signal for producing a variable current related to both said periodic voltage and said radiant signal, said variable light sensitive resistor producing said variable current in phase alignment with said periodic voltage wherein said phase alignment is independent of said amplitude;

radiant energy emitting means for emitting said radiant signal in proportion to an electronic signal;

current summing means coupled to the medium and said current generating means and said variable resistor for summing said negative current and said variable current and said resistive current component and said capacitive current component;

sampling means for sampling said summed current over a time period in phase with said resistive current component;

averaging means coupled to said sampling means for averaging said capacitive current component to zero and for averaging said resistive current component plus said variable current less said negative current to define said electronic signal;

means for coupling said electronic signal to said variable resistor so that said variable current less said negative current is substantially equal to said resistive current component and $\pi$ radians out of phase with said periodic voltage and said resistive current component thereby nulling said resistive current component from said summed current; and detecting means coupled to said summing means and in phase with said capacitive current component for detecting said capacitive current component independently of said resistive current component.

2. The apparatus recited in claim 1 wherein said periodic voltage comprises a triangular wave having zero crossing points every $\pi$ radians.

3. The apparatus recited in claim 2 wherein said capacitive current component substantially comprises a square wave.

4. The apparatus recited in claim 3 wherein said averaging time period coincides with said triangular wave zero crossings.

* * * * *